US00PP36316P2

(12) United States Plant Patent
Bennett

(10) Patent No.: US PP36,316 P2
(45) Date of Patent: Dec. 17, 2024

(54) ***ROSA HYBRIDA* SHRUB PLANT NAMED 'AUSA6B15'**

(50) Latin Name: *Rosa hybrida*
Varietal Denomination: AUSA6B15

(71) Applicant: David Austin Roses Ltd., Wolverhampton (GB)

(72) Inventor: Carl Bennett, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 18/445,835

(22) Filed: Feb. 27, 2024

(51) Int. Cl.
*A01H 5/02* (2018.01)
*A01H 6/74* (2018.01)

(52) U.S. Cl.
USPC ..... Plt./104

(58) Field of Classification Search
USPC ..... Plt./101, 102, 104
See application file for complete search history.

(56) References Cited

PUBLICATIONS

CPVO Register. 2024. https://online.plantvarieties.eu/public-ConsultationDetails?registerId=20232347&denomination=ausb18a15. 2 pages. (Year: 2024).*

* cited by examiner

*Primary Examiner* — Karen M Redden
(74) *Attorney, Agent, or Firm* — KPPB LLP

(57) ABSTRACT

A variety of rose plant of the shrub class, named 'AUSA6B15'. The 'AUSA6B15' is a variety of a rose with yellow medium-sized, cupped blooms having a medium, fruity fragrance in a medium-sized, upright and bushy shrub.

1 Drawing Sheet

Classification: The present invention relates to a new *Rosa hybrida* shrub of the market class 'English Rose'.

Variety denomination: The new plant has the varietal denomination 'AUSA6B15'.

Origin of invention: This invention relates to a new and distinct variety of shrub rose plant named 'AUSA6B15', which was originated from the cross-pollination of the two 'unnamed' and unpatented seedlings of *Rosa hybrida*.

BACKGROUND OF THE INVENTION

The primary objective of this breeding was to produce a rose with yellow medium-sized, cupped blooms having a medium, fruity fragrance in a medium-sized, upright and bushy shrub.

SUMMARY OF THE INVENTION

Among the features which distinguish the new variety from others presently available and commercial rose cultivars known to the inventor is the following combination of characteristics: medium-sized yellow blooms with a medium, fruity fragrance with hints of lemon, forming a shapely shrub with an upright and bushy shape capable of repeat flowering.

Asexual reproduction of the new variety by budding as performed in Albrighton, United Kingdom shows that the foregoing and other distinguishing characteristics come true to form and are established and transmitted through succeeding asexual propagations. 'AUSA6B15' may be asexually propagated by budding. The budding successfully occurred on an unpatented plant/rootstock *Rosa dumetorum* 'Laxa' for the observed plants.

COMPARISON WITH PARENTS

The maternal and paternal parents of 'AUSA6B15' are two unnamed seedlings. The new rose may be distinguished from its seed parent, by the following combination of characteristics: the seed parent has a higher petal count and is less disease resistant when compared to 'AUSA6B15'. The new rose may be distinguished from its pollen parent, by the following combination of characteristics: the pollen parent has a pink color when compared to 'AUSA6B15', which is yellow and shows a different growth habit.

COMPARISON WITH THE CLOSEST COMMERCIALLY AVAILABLE CULTIVAR

The most similar rose variety is 'AUSeasel' (not patented). Both blooms are similar in color, however, 'AUSeasel' has a larger flower diameter (approx. 8 cm) when compared to 'AUSA6B15' (approx. 6 cm). 'AUSA6B15' also has a different number of prickles, with 'AUSA6B15' having many-medium reddish prickles, while 'AUSeasel' has few-medium yellowish prickles. Finally, anthocyanin coloration of the leaf is present in 'AUSA6B15', but is absent in 'AUSeasel'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

Observations of budded 'AUSA6B15' specimens were made at a garden in Albrighton, Wolverhampton, United Kingdom. The following description is of 7-year-old rose plants of the new variety grown in a garden environment in Albrighton, United Kingdom in the month of June. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

*Size*.—About 2.5 cm long and 2 cm in diameter when the petals start to unfurl.

*Form*.—The bud form is pointed ovoid.

*Color*.—When sepals first divide, the bud color is RHS 13B (yellow group), deepening to RHS 25C (orange group) at the tip. When half blown, the upper sides of the petals are RHS 10C (yellow group).

*Calyx*.—Shape: star shape, with the sepals folding back against the stems. Length: 5.9 cm. Diameter: 5.9 cm.

*Sepals*.—Arrangement: Regular. Color: Upper Surface: RHS 143C (green group). Lower Surface: RHS 144A (yellow-green group) with a central flash of approximately RHS 53B (red group). Length: 2.5 cm. Width: 1 cm. Shape: Lanceolate. Apex: Overall shape, lanceolate. Margin: Smooth and very slightly hairy. Surface texture: Upper Surface: Smooth and hairy. Lower Surface: Smooth. Number: There are 3 normally appendaged sepals, and 2 unappendaged sepals with smooth/slightly hairy edges.

*Receptacles*.—Color: RHS 144A (yellow-green group). Shape: Apple. Size: Medium, about 1.15 cm long×0.9 cm wide. Surface: Smooth.

*Peduncle*.—Length: Short, averaging about 5.3 cm. Surface: Smooth. Color: RHS 144A (yellow-green group) to RHS 144B (yellow-green group). Strength: Strong.

Blooms:

*Type*.—Cupped.

*Size*.—Medium, average open diameter is about 6 cm and average depth is about 3.25 cm.

*Borne*.—Several together in clusters of 10-14 with blooms having an irregular shape.

*Penduncle*.—Strength: Strong, average length is about 5.3 cm. Diameter: 0.2 cm.

*Form*.—When first open, bloom is globular. Permanence of bloom: Retains its form to the end and outer petals curl back.

*Upper profile*.—Flattened convex.

*Lower profile*.—Convex.

Petalage: Number of petals under normal conditions: 33.

*Color*.—The upper sides of the petals are RHS 10A (yellow group). The reverse sides of the petals are RHS 10B (yellow group). The base of the petals has a medium basal spot of RHS 9B (yellow group).

*Variegations*.—None.

*Discoloration*.—The general tonality at the end of the first day is RHS 15B (yellow-orange group), and at the end of the third day is RHS 10C (yellow group).

*Fragrance*.—Moderate. Character of fragrance: fruity.

Petals:

*Texture*.—Smooth, satiny and thin on both sides.

*Size*.—Width: 3.15 cm. Length: 3.5 cm.

*Surface*.—Smooth.

*Shape*.—Obcordate with a rounded base.

*Margin*.—Mostly entire, with a slight notch in the center of the apex.

*Apex shape*.—Obcordate.

*Base shape*.—Rounded.

*Form*.—Incurved.

*Arrangement*.—Regularly arranged.

*Petaloids*.—Number: 0-5. Color: RHS 10A (yellow group). Length: 2 cm. Width: 1 cm. Shape: Irregular. Margin: Uniform.

*Persistence*.—Petals drop off cleanly before drying.

*Lastingness*.—On the plant: fair about 5 days. As a cut flower: not tested.

Reproductive parts:

*Stamens*.—Number: approximately 70-75. Length: approximately 1.5 cm.

*Anthers*.—Length: approximately 0.2 cm. Color: RHS 13B (yellow group). Arrangement: Regular around styles with some tucked in calyx or partly so.

*Filaments*.—Color: RHS 13B (yellow group). Length: 1.2-1.3 cm.

*Pollen*.—Color: RHS 9B (yellow group). Amount: Scarce.

*Pistils*.—Number: approximately 40. Length: approximately 0.6 cm.

*Styles*.—Color: RHS 155C (white group). Length: 0.5 cm.

*Stigmas*.—Color: RHS 12A (yellow group) at the top, with RHS 48A (red group) at the bottom. Length: approximately 0.1 cm.

*Hips*.—NONE Observed.

PLANT CHARACTERISTICS

Plant form: Shrub.

Plant growth: Medium and upright.

Age to maturity: 2 years.

Mature plant: Height: 110 cm. Width: 125 cm.

Rootstock: '*Rosa dumetorum* 'Laxa' (not patented) for the observed plants in the United Kingdom. 'Dr Huey' (not patented) in the USA.

Foliage:

*Number*.—Leaflets on normal mid-stem leaves is: 5, sometimes 7 (including terminal leaflet).

*Size*.—Medium, about 14.2 cm long×10 cm wide.

*Quantity*.—Abundant/normal. Number of leaves per flowering stem is: approximately 6-10.

*Color*.—New foliage: Upper side: RHS 146B (yellow-green group) at center, blending to RHS 184B (grayed-purple group). Lower side: RHS 59B (red-purple group). Old foliage: Upper side: RHS 147A (yellow-green group). Lower side: RHS 191A (grayed-green group).

*Glossiness*.—Weak/very weak.

Leaflets:

*Size*.—About 5.1 cm long×3.5 cm wide.

*Shape*.—Pointed oval.

*Base shape*.—Rounded.

*Apex shape*.—Acuminate.

*Edge*.—Serrated.

*Serrations*.—Some double/mostly single.

*Petiole*.—Color: upper side is RHS 144A (yellow-green group). Upper Surface Texture: Smooth. Underside: Slightly glandular.

*Petiole rachis*.—Color: RHS 144A (yellow-green group), with some RHS 59A (red-purple group) on the central upper area. Underside: smooth with prickles. Lower Surface Texture: smooth.

*Stipules*.—Length: 3.2 cm. Shape: Lateral. Descriptor: smooth/glandular edges. Apex: Acute. Color: RHS 144B (yellow-green group).

*Auricle*.—Shape: Lanceolate. Length: 1 cm. Width: 0.4 cm. Color: RHS 144B (yellow-green group).

*Vein color*.—RHS 147A (yellow-green group).

*Venation pattern*.—Reticulate.

Wood:

*New wood*.—Color: RHS 146B (yellow-green group) at the top and RHS 184B (grayed-purple group) at the bottom. Bark: Smooth.

*Old wood*.—Color: RHS 146C (yellow-green group) with small spots of RHS 173B (grayed-orange group). Bark: Smooth.

Branching habit:

*Number*.—2-3 per main stem.

*Dimensions*.—Length: 85 cm. Diameter: 0.9 cm.

Stems:

*Mature stem*.—Length: approximately 100 cm. Diameter: 0.9 cm.

*Internode distance*.—Approximately 7.9 cm. The above measurements are all variable, depending on growing conditions in a season.

*Stem pubescence present*.—No.

Prickles:

*Quantity*.—On main canes from base: many/ordinary. Number per stem length: 18 per 20 cm. On laterals from main canes: many/ordinary. Number per stem length: 18 per 20 cm.

*Form*.—Hooked downward/deep concave.

*Length*.—0.9 cm.

*Color when young*.—RHS 59A (red-purple group).

*Color when mature*.—RHS 59A (red-purple group), paling to a tip of RHS 159A (orange-white group).

Small prickles:

*Quantity*.—Main stalk: Many/ordinary. Number per stem length: 15 per 20 cm. Laterals: Many/ordinary. Number per stem length: 15 per 20 cm.

*Color*.—When young: RHS 59A (red-purple group). When mature: RHS 59A (red-purple group).

Disease resistance:

*Powdery mildew* (*Podosphaera pannosa*).—Resistant.

*Downy mildew* (*Peronospora species*).—Resistant.

*Blackspot* (*Diplocarpon rosae*).—Resistant.

*Rust* (*Phragmidium tuberculatum*).—Resistant.

Pest resistance: Not tested.

Winter hardiness: Not tested.

Growing conditions: Normal garden conditions.

What is claimed is:

1. A new and distinct variety of rose plant of the shrub class, named 'AUSA6B15', substantially as herein shown and described.

* * * * *

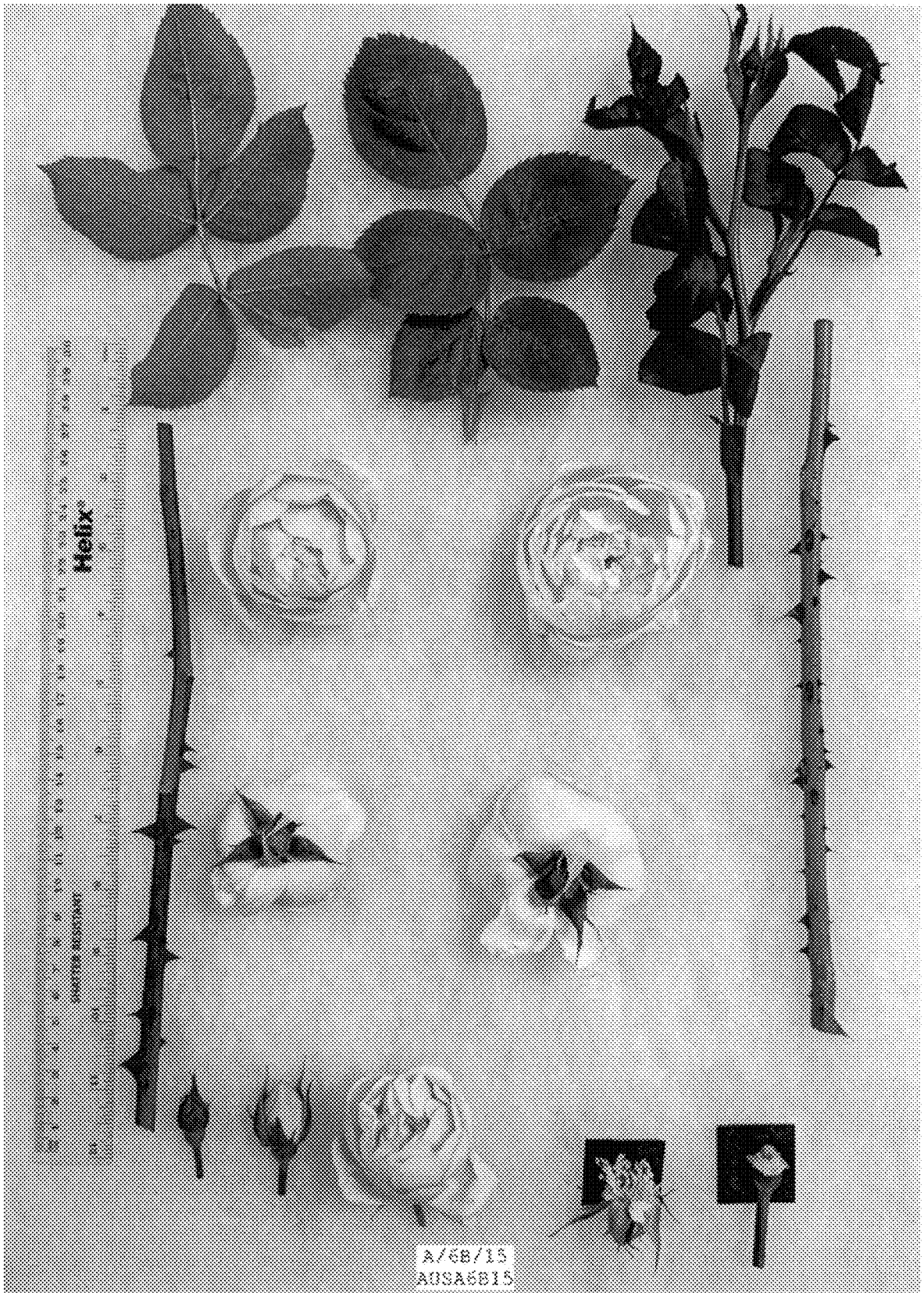
Helix
A/68/15
A0SA5B15